United States Patent [19]

Sakurai et al.

[11] Patent Number: 5,641,868
[45] Date of Patent: Jun. 24, 1997

[54] INTERLEKIN-6 COMPOSITIONS, AND A PRODUCTION PROCESS THEREOF

[75] Inventors: Shingou Sakurai, Mishima; Masanobu Naruto, Kamakura; Makoto Kihara, Mishima; Keizo Hanada; Emiko Sano, both of Yokohama; Shigeru Ichikura, Mishima; Jun Utsumi, Kamakura; Kazuo Hosoi, Sunto-gun, all of Japan

[73] Assignee: Toray Industries, Inc., Tokyo, Japan

[21] Appl. No.: 427,862

[22] Filed: Apr. 26, 1995

Related U.S. Application Data

[63] Continuation of Ser. No. 962,204, filed as PCT/JP92/00487, Apr. 17, 1992, abandoned.

[30] Foreign Application Priority Data

Apr. 18, 1991 [JP] Japan ..................................... 8660291
Apr. 19, 1991 [JP] Japan ..................................... 3-088284

[51] Int. Cl.$^6$ .............. C07K 1/16; C07K 14/54; C12P 21/00; A61K 38/20
[52] U.S. Cl. ............. 530/412; 424/85.2; 435/69.52; 530/351; 530/413; 530/415
[58] Field of Search ................... 424/85.2, 85.6; 435/69.5, 69.51, 69.52, 70.4, 240.1, 240.2, 240.3, 240.31, 70.5; 514/8, 12, 21; 530/351, 412, 413, 415

[56] References Cited

U.S. PATENT DOCUMENTS

| | | | |
|---|---|---|---|
| 4,100,150 | 7/1978 | Cartwright | 530/351 |
| 4,314,935 | 2/1982 | Uemora et al. | 530/351 |
| 4,658,017 | 4/1987 | Dembinski et al. | 530/351 |
| 4,680,261 | 7/1987 | Nobuhara et al. | 435/705 |
| 4,913,812 | 4/1990 | Moriguchi et al. | 210/198.2 |
| 5,004,605 | 4/1991 | Hershenson | 424/85.6 |

FOREIGN PATENT DOCUMENTS

| | | |
|---|---|---|
| 0220574 | 5/1987 | European Pat. Off. . |
| 0257406 | 3/1988 | European Pat. Off. . |
| 63-150297 | 6/1988 | Japan . |
| 8800206 | 1/1988 | WIPO . |

OTHER PUBLICATIONS

May et.al. "On The Multimeric Nature of Natural Human Interleukin-6" J.Biol. Chem 266 (15) 9950–9955 1991.

Parekh, et. al. "Glycosylation of Interleukin-6 Purified From Normal Human Blood Mononuclear Cells" Eur.J.Biochem 203 135–141 1992.

May et.al. "Synthesis & Secretion of Multiple Forms of $\beta_2$–Interferon/B Cell Differentiation Factor 2/Hepatocyte–Stimulating Factor by Human Fibroblasts & Monocytes." J.Biol.Chem 263 (16) 7760–66 1988.

Schiel et.al. "Microheterogeneity of Human Interleukin–6 Synthesized by Transfected MH/3T3 Cells: Comparison w/ Human Monocytes, Fibroblasts & Endothelial Cells" Eur J Immunol. 20 883–887 1990.

Van Damme, et.al. "Purification & Characterization of Human Fibroblast Derived Hybridoma Growth Factor Identical to T–Cell Derived B–Cell Stimulatory Factor 2 (Interleukin 6)" EurJ.Bioch. 168 543–550 1987.

Arcone et.al. "Single Step Purification & Structural Characterization of Human Interleukin 6 Produced in *E. coli* from a T7 RNA Polymerase Expression Vector" EurJ.Bioch. 198 541–547 1991.

Sofer et.al. "Designing an Optical Chromatographic Purification Scheme" BioTechniques 198–203 1983 (Nov./Dec.).

Leong "Production & Purification of Natural Human $\beta$ Interferon" in Pfeffer Mechanisms of Interferon Actions pp. 45–60 1987.

Kishimoto, T. "The Biology of Interleukin–6", Blood 74: 1–10, 1989.

Rosen et al. eds. Dictionary of Immunology, MacMillan Press, 1989.

*Primary Examiner*—Mindy Fleisher
*Assistant Examiner*—Nancy J. Degen
*Attorney, Agent, or Firm*—White & Case

[57] ABSTRACT

The present invention relates to compositions containing human interleukin-6 with sugar chains, a process for preparing human interleukin-6 by culturing cells in a medium containing ascorbic acid or any of its derivatives, and a process for purifying a crude raw human interleukin-6 solution by chromatography using a carrier with heparin bound. The present invention has allowed the production of high quality human interleukin-6 compositions with sugar chains, and their application to medicines. Furthermore, it has established a process for massproducing human interleukin-6.

8 Claims, No Drawings

INTERLEKIN-6 COMPOSITIONS, AND A PRODUCTION PROCESS THEREOF

This application is a continuation of application Ser. No. 07/962,204 filed Feb. 5, 1993, now abandoned.

The present invention relates to interleukin-6 (hereinafter abbreviated as IL-6) compositions, and a production process thereof. In more detail, the present invention relates to human IL-6 compositions with sugar chains useful as medicines and a process for massproducing them at high quality.

BACKGROUND ARTS

IL-6 is the standardized name of a cytokine called *B lymphocyte* differentiating factor, interferon $\beta_2$, 26 Kd protein, hybridoma/plasmacytoma growth factor, hepatocyte stimulating factor, etc.

IL-6 induces activated B cells to be differentiated into antibody forming cells. For T cells, IL-6 induces T cells stimulated by mitogens to produce IL-2 and induces the expression of IL-2 receptor on a certain T cell line or thymocytes. For blood forming cells, IL-6 induces the growth of blood forming stem cells synergistically in the presence of IL-3. Furthermore, recently, it was reported that IL-6 acted like thrombopoietin. As stated here, IL-6 has a variety of biological activities and is expected to be useful for clinical application.

IL-6 is produced by various cells. It is produced by lymphocytes and is also produced by human fibroblasts stimulated by Poly (I).Poly (C) and cycloheximide (Eur. J. Biochem., 159, 625, (1986)). Murine IL-6 is produced in mouse cells, which are stimulated by Poly (A).Poly (U) (Immunopharmacology, 21, p. 33, (1991)). Inducers for stimulation are diverse, and those include known cytokines such as IL-1, TNF and IFN-$\beta$, growth factors such as PDGF and TGF-$\beta$, LPS, PMA, PHA, cholera toxin, etc. (Science, 235, 731 (1987)). Moreover, it is reported that human vascular endothelial cells, macrophages, human glioblastomas, etc. also produce IL-6 (Immunol.,142,144, (1989), J. Immunol., 141, 1529, (1988), Japanese Patent Laid-Open No. 88-296688)). Furthermore, it is also known that the productivity can be further enhanced by stimulating cells using an inducer and subsequently treating the cells by a metabolic inhibitor such as verapamil, cycloheximide or actinomycin D, etc. (J. Immunol., 144, 4242–4248 (1990)). However, how IL-6 is different in activity, structure, etc. due to the differences in producing cells, inducing substance, etc. is unknown. To effectively utilize IL-6 as a medicine at least, it is necessary to develop a mass production system and to clarify the physical properties and biological activities of produced IL-6. However, no process for efficient mass production of high-quality IL-6 containing sugar chains useful for clinical application has been established yet.

It is known that IL-6 can be purified by letting CPG (controlled pore glass) adsorb it in batch operation, recovering it by an acid and using a polyclonal antibody column, gel permeation chromatography, ion exchange chromatography and reverse phase high performance liquid chromatography using a C1 column in combination (Eur. J. Biochem., 168, 543 (1987)) or by using membrane concentration, gel filtration chromatography, dialysis, ion exchange chromatography, FPLC and reverse phase high performance liquid chromatography (HPLC) in combination (Proc. Natl. Acad, Sci. USA, 82, 5490 (1985)). Recombinant IL-6 derived from *Escherichia coli* is purified by using urea treatment, dialysis, guanidine hydrochlorate treatment, gel filtration chromatography and ion exchange chromatography in combination (Tosoh Research Report, Vol. 32, No. 2 (1988)). Furthermore, human BCDF produced by *Escherichia coli* can be purified to a protein purity of 99% or more and an endotoxin content of 0.6 EU/mg protein or less, by two-stage reverse phase HPLC using chemical bond type ($C_8$) silica gel as a packing material(Japanese Patent Laid-Open No. 90-186996). However, these conventional purification processes are complicated and not suitable for mass processing for industrial production. In addition, reverse phase HPLC conditions are not mild for proteins, and are liable to cause denaturation or association of proteins, being not adequate for obtaining high quality IL-6 product.

As described above, the industrial utilization of IL-6 as a medicine is possible only after successful mass production of high quality IL-6 product and the clarification of its properties. The present invention solves these problems and provides a process to produce glycosylated IL-6 compositions in high quality under the control of good manufacturing process.

DISCLOSURE OF THE INVENTION

The present invention provides human IL-6 compositions with sugar chains and specified certain properties, and an effective production process thereof. Concretely it provides a process for preparing a human IL-6 composition, by culturing human IL-6 producing cells, comprising the step of adding ascorbic acid or any of its derivatives to the medium, and a process for preparing IL-6, comprising the step of purifying a crude raw IL-6 solution by chromatography using a carrier with heparin combined (hereinafter called the heparin carrier).

THE MOST PREFERRED EMBODIMENT OF THE INVENTION

A human IL-6 composition of the present invention contains natural human IL-6 with sugar chains, and is characterized by (1) containing two components of, at least, 22000 to 25000 and 26000 to 30000 in molecular weight in terms of SDS-PAGE by 60 to 90% and 40 to 10% respectively, (2) containing at least three sequences of Pro-Val-Pro-Pro-Gly-, Val-Pro-Pro-Gly-Glu and Ala-Pro-Val-Pro-Pro- as terminal amino acid sequences, identified respectively as SEQ ID NO: 1, SEQ ID NO: 2 and SEQ ID NO: 3 in the Sequence Listing, and containing Val-Pro-Pro-Gly-Glu- (SEQ ID NO:2) by 40% or more (preferably 50% or more), and (3) containing mannose, fucose, galactose, N-acetylglucosamine, N-acetylgalactosamine and N-acetylneuraminic acid as component sugars.

These properties represent high quality properties for IL-6 to sufficiently exhibit its proper biological activities, and with these properties, the IL-6 is expected to be more stable and to have lower antigenecity when administered in vivo compared to the non-glycosylated IL-6. A human IL-6 composition in conformity with these conditions can be industrially produced by the mass culture process and mass purification process described below.

IL-6 is produced constantly by various cells or by various types of stimulation. It can also be produced by genetic recombinant cells.

IL-6 with sugar chains is produced by not only non-adherent cells in culture such as T cells, B cells and monocytic macrophages, but also adhesion dependent cell lines in culture such as fibroblasts, osteosarcoma cells, lung cancer cells and vascular endothelial cells. In the present invention, however, adhesion dependent cells can be preferably used as IL-6 producing cells. Especially fibroblasts can be preferably used.

Furthermore, as IL-6 producing cells of the present invention, recombinant cells such as recombinant CHO cells can also be used. Recombinant cells also include non-adherent cells and adhesion dependent cells, depending on host cells, and in the present invention, adhesion dependent cells can be preferably used.

According to the present invention, high quality IL-6 with sugar chains can be produced at a high yield by culturing IL-6 producing cells. The present invention provides a process for preparing IL-6, in which IL-6 is constantly produced by culturing floating cells or adhesion dependent cells without using any inducer, or is produced by stimulating the production by any of various IL-6 inducers, or is produced by recombinant cells, comprising the step of adding ascorbic acid or ascorbic acid derivatives to the medium, for increasing the production.

Adhesion dependent cells can be preferably cultured by using a Roux bottle or roller bottle, or by letting them adhere to a microcarrier or hollow fibers, or fixing them to microcapsules. Among them, the use of microcarrier, hollow fibers or microcapsules is preferable.

A preferable microcarrier has a matrix made of a synthetic resin such as collagen, gelatin, cellulose, crosslinked dextran or polystyrene, and has charged groups such as dimethylaminopropyl, dimethylaminoethyl or trimethylhydroxyaminopropyl groups added. A microcarrier with the matrix material coated with collagen or gelatin can also be used. Marketed microcarriers include "Cytodex-1" with dimethylaminoethyl added to crosslinked dextran (produced by Pharmacia) and "Cytodex-3" with crosslinked dextran coated with denaturated collagen (produced by Pharmacia). As hollow fibers, those formed by modified cellulose are available, and for example, "Vitafiber" (produced by Amicon) is available on the market. Microcapsules are prepared by using collagen or sodium arginate capable of forming a water permeable gel, with cells embedded inside (Bio/technol., 1, 736 (1983)).

IL-6 producing cells can be treated to produce IL-6 by an inducer such as a natural or synthetic RNA, or cytokine such as IL-1, TNF or IFN-β, or growth factor such as PDGF or TGF-β, PMA, PHA, lipopolysaccharide or cholera toxin, etc. (Science, 235, 731 (1987)). Among them, the use of Poly (I).Poly(C) as a synthetic RNA is preferable. Furthermore, it is also possible to treat the cells by a metabolic inhibitor such as verapamil, cycloheximide or actinomycin D, etc. after stimulating the cells using an inducer, for further promotion of production (J. Immunol., 144, 4242–4248 (1990)).

The present invention comprises the step of adding ascorbic acid or any of its derivatives to the medium where IL-6 producing cells are cultured. The time when ascorbic acid or any of its derivatives is to be added is not especially limited, but if IL-6 is produced using an inducer, it is preferable to add ascorbic acid or derivative to the IL-6 producing medium, i.e., when IL-6 is produced after stimulating using an inducer after growth of IL-6 producing cells. Ascorbic acid or any of its derivatives should be added preferably by 0.05 to 10 mM, more preferably by 0.5 to 3 mM. The ascorbic acid used for culturing should be preferably a derivative stable under culturing conditions and acting like ascorbic acid. The ascorbic acid derivative can be preferably selected from L-ascorbic acid phosphates (Hata, et al., 1988, Summaries of 35th Meeting of Research on Collagen, p. 85 to 89) and glucoside L-ascorbate.

The medium used in the present invention can be any usually marketed one, and it is preferable to select a medium suitable for the cells, from the marketed media or those modified. For example, Eagle MEM, RPMI1640, α-MEM and their modified media can be preferably used. The dissolved oxygen concentration and pH in the medium should be preferably controlled within the ranges suitable for the cells. The dissolved oxygen concentration should be preferably kept in a range from 20 to 80%, more preferably 40 to 65% of the saturated solubility to air. Similarly, pH should be preferably controlled in a range from 7.0 to 8.0

To produce IL-6 with sugar chains, it is preferable to add sugars for avoiding the shortage of sugars in the medium. The sugars generally used include glucose, maltose, etc. Especially to avoid the shortage of sugars in the IL-6 producing medium, it is preferable to add once to several times per day or to add continuously. For example, glucose should be preferably kept at a concentration of 0.1 to 2.5 g/l, more preferably 0.2 to 1.5 g/l in the medium.

The human IL-6 in the crude solution produced can be confirmed by the enzymelinked immunosorbent assay (ELISA) and HPGF (hybridoma/plasmacytoma growth factor) activity measurement, etc.

Before bringing the crude IL-6 solution obtained like this into contact with the heparin carrier, it is preferable to preconcentrate the crude IL-6 by using a silica based adsorbent (hereinafter abbreviated as the silica carrier), etc. according to any conventional method (J. Exp. Med., 165, 914 (1987). The Biology of the Interferon System, 1988, p. 395, etc.). The silica carrier can be preferably selected from "CPG" (controlled pore glass) or silica beads, etc., for example, "CPG" (produced by Sigma), "Microbeads Silica Gel" (produced by Fuji Devision), etc. The preconcentrated IL-6 solution can be in succession fed through a cation exchanger, to remove foreign matters by adsorption, for further raising the purity. The cation exchanger in this case refers to a carrier with carboxyl groups, sulfonate groups or phosphate groups, etc. combined to an insoluble skeletal carrier such as a polysaccharide based carrier or synthetic polymer based carrier made of cellulose or agarose, etc. It can be selected, for example, from "S Sephalose FF" (produced by Pharmacia), "CM Sephalose CL-6B" (produced by Pharmacia), etc.

The heparin carrier used in the present invention can be any carrier with heparin combined to an insoluble skeletal carrier such as a polysaccharide based carrier or synthetic polymer based carrier made of cellulose or agarose, etc., and can be selected, for example, from "Heparin Toyopearl" (produced by Tosoh) and "Heparin Cellulofine" (produced by Chisso).

When the crude IL-6 solution is brought into contact with the heparin carrier, it is desirable to adjust its pH to 5–10. Especially preferably, the pH should be in a range from 5.5 to 8.0 in which the affinity to heparin can be sufficiently secured, and the ionic strength is recommended to be 0.3 or less. The IL-6 adsorbed by the heparin carrier like this can be recovered by raising the ionic strength. For example, it can be recovered by using a liquid prepared by adding an inorganic salt such as sodium chloride or ammonium sulfate to a buffer such as sodium phosphate buffer. For recovering IL-6, the salt concentration can be increased in a gradient or stepwise. The ionic strength should be 0.3 to 2, preferably 0.3 to 1.

Furthermore, for enhancing the purity, it is effective to use a carrier with hydrophobic groups combined hereinafter abbreviated as the hydrophobic carrier). If the IL-6 solution treated by the heparin carrier has a salt added or set in an acid condition, the hydrophobic carrier can efficiently adsorb IL-6. The adsorption method can be either column method or batch method.

The hydrophobic carrier used here can be any carrier with alkyl groups ($C_1$ to $C_{18}$), phenyl groups, octyl groups, etc. chemically combined to the skeletal carrier, but a carrier with phenyl groups or butyl groups is especially desirable. The skeletal carrier can be an insoluble carrier such as a polysaccharide based carrier or synthetic polymer based carrier made of cellulose or agarose, etc. The hydrophobic carrier used can be selected, for example, from "Butyl Toyopearl" (produced by Tosoh), "Phenyl Cellulofine" (produced by Chisso), etc. The adsorption is caused by adding a salt such as sodium sulfate, potassium sulfate, ammonium chloride, potassium chloride or sodium chloride to the IL-6 solution at a high concentration. A preferable adsorption condition using sodium chloride is 0.2 to 5M and/or pH 2 to 7.5. IL-6 can be recovered from the hydrophobic carrier by lowering the salt concentration in a gradient or stepwise according to any conventional method. In addition to lowering of salt concentration, the change of pH or temperature may be effective, depending on conditions. This hydrophobic chromatography allows IL-6 to be efficiently eluted, for example, by lowering the salt concentration at pH 5 to 9, for separation from unwanted proteins. Any of various solutions not causing the elution of IL-6 can be used to wash the IL-6 adsorbed carrier for removing unwanted proteins. For example, a neutral buffer rather lowered in adsorption ionic strength or an acid solution of about pH 2 with remarkably low salt concentration can be used to remove unwanted proteins.

When the hydrophobic carrier is used, the heparin carrier and the hydrophobic carrier can be used in either order, but it is preferable to use the hydrophobic carrier after using the heparin carrier in view of the composition of the solution.

The IL-6 obtained by the above purification method including the heparin carrier was 95% or more in purity in the analysis using reverse phase high performance liquid chromatography.

The purification process described for the present invention can be applied not only to the IL-6 produced by animal cells but also to the human IL-6 obtained by the recombinant cells using *Escherichia coli*, yeast or insect cells, etc. as the host.

To formulate the IL-6 composition obtained in the present invention, it is preferable to use human serum albumin, proper surfactant or sugar, etc. as a stabilizer. It is also possible to add a proper sugar or amino acid, etc. as an excipient, for making a freeze dried preparation. Furthermore, it is possible to sterilely filter the solution, for use as an injection, or to prepare an ointment, suppository or tablets, etc. using a pharmaceutical base.

The human IL-6 of the present invention can be determined by ELISA using a monoclonal antibody with neutralization activity (Biochem. Biophys. Res. Commun., 165, 728–734 (1989)), or by using human B cell line CL4 capable of reacting with human BCDF to produce IgM (Proc. Natl. Acad. Sci., 82, 5490 (1985)), or by using mouse hydriboma cell line 7TD1 (Proc. Natl. Acad. Sci. USA., 83, 9678–9683 (1986)), etc.

EXAMPLES

The present invention is described below concretely in reference to examples, but is not limited thereto or thereby.

Example 1

On one liter of an Eagle MEM medium containing 5% of neonatal calf serum in a 2-liter glass culture tank, human fibroblasts were cultured on a microcarrier [Microcarrier: "Cytodex 1" (produced by Pharmacia), 37° C.] upto $10^6$ cells/ml. Then, the medium was replaced by one liter of a serum-free Eagle MEM medium containing a small amount of carboxymethyl cellulose, and 100,000 units/liter of human natural interferon-β (IFN-β) was added as priming agent. On the following day, furthermore, 10 mg/liter of Poly (I).Poly (C) was added, as an inducer. Two hours later, the producing medium was replaced by an Eagle MEM medium containing a small amount of methyl cellulose. Subsequently for 6 days, culture was continued at 37° C. in that condition.

Stirring was stopped to allow the microcarrier to settle, and the supernatant solution was filtered, and the filtrate was put into an 1 liter container. Silica carrier ["Microbeads Silica Gel" (produced by Fuji Devison)] was sterilized at a high pressure at 121° C. for 30 minutes in sodium phosphate buffer, and 4 ml each of it was packed into two columns which were connected in series. Through them, the produced filtrate was fed at a flow velocity of 20 ml/hr. After completion of feeding all the quantity, the two columns were subjected to chromatography separately. Through them, 25 ml of sodium phosphate buffer was passed respectively for washing, and 20 mM hydrochloric acid was fed to recover 10 ml each of fractions containing human IL-6. To the solutions recovered with hydrochloric acid, 0.3M disodium hydrogenphosphate aqueous solution was added, to adjust pH to 6.4. The precipitates produced were removed by centrifugation at 3000 rpm at 4° C. for 30 minutes.

Each of the supernatant solutions was fed through a column packed with 1 ml of "AF-Heparin Toyopearl 650M" (produced by Tosoh) as heparin chromatography carrier, for adsorption. Each of the columns was washed by 10 mM sodium phosphate buffer(pH 6.4), and 2 ml of a fraction containing human IL-6 was eluted with 20 mM sodium phosphate buffer containing 0.3M NaCl (pH 7.2). At this moment, the respective fractions were pooled. Furthermore, 4M sodium chloride was added, to adjust the entire salt concentration to be 2.15M. Then, the fractions was fed through a column packed with 1 ml of "Butyl Toyopearl 650M" (produced by Tosoh), for adsorption. The temperature at the time of adsorption was 23° C. Then, the columns were respectively washed by a buffer containing 2M NaCl (pH 7.2), 20 mM HCl containing 2M NaCl (pH1.8), 20 mM HCl (pH 1.8), 0.5M sodium phosphate buffer (pH 5.8) and 0.05M sodium phosphate buffer (pH 5.8) in this order, and finally 50 mM sodium phosphate buffer (pH 7.2) was fed for recovery. The purified human IL-6 obtained like this was 95% or more in protein purity (evaluation by $C_{18}$ reverse phase high performance liquid chromatography), and the yield against the crude produced solution was 30%.

The concentration of human IL-6 was determined by ELISA using a 96-hole plate. That is, the plate was coated with anti-IL-6 monoclonal antibody at a concentration of 1 µg/ml. Blocking was achieved by sodium phosphate buffer containing bovine serum albumin (BSA) (pH 7.0 washing buffer). At first, 50 µl of 10 µg/ml goat anti-IL-6 antibody as a secondary antibody labelled by biotin was placed on the plate, and furthermore, respectively 100 µl of IL-6 standard solution known in concentration and IL-6 solution unknown in concentration were added. Reaction was executed by shaking for 1 hour. The reaction product was washed by the washing buffer 3 times, and 100 µl of "Streptoabidin-HRP Conjugate" (produced by BRL) diluted to 2000 times by the washing buffer was added. Reaction was executed for 30 minutes. The plate was washed with the washing buffer 3 times, and 100 µl of citrate buffer containing orthophenylenediamine and hydrogen peroxide (pH 5.0) was added, to cause coloring reaction. Thirty minutes later, the reaction was stopped by 4.5N sulfuric acid, and the absorbance of the respective wells were measured at 492 to 690 nm using a photometer for microplate ("Multiscan CM" produced by Flow Laboratory).

Example 2

Three lots of purified human IL-6 products were prepared as done in Example 1. The purified products (about 5 μg) were subjected to SDS-PAGE (5–20% gradient gel) in a reducing condition. After completion of electrophoresis, the gels were dyed by Coomassie Brilliant Blue, and two bands of 22000 to 25000 and 26000 to 30000 in molecular weight were detected as main components. The existence ratio of the bands determined by a chromato-scanner was 75±15%: 25±15%.

Ten micrograms each of the respective purified products were analyzed on N-terminal amino acid sequence, and from all the products, Val-Pro-Pro-Gly-Glu- (SEQ ID NO:2) was detected as the main component, and furthermore, at least two components of Pro-Val-Pro-Pro-Gly- (SEQ ID NO:1) and Ala-Pro-Val-Pro-Pro- (SEQ ID NO:3) were contained as sub-components.

Furthermore, about 30 μg each of the respective purified products were analyzed on sugar composition, and from all the products, mannose, fucose, galactose, glucosamine, galactosamine and N-acetylneuraminic acid were detected as component monosaccharides. As for amounts, 0.2 mole or more of fucose and 0.5 mole or more each of other monosaccharides were contained per 1 mole of protein.

Example 3

Two liters of an Eagle MEM medium containing 5% of fetal bovine serum and 3 g/l of crosslinked dextran microcarrier with diethylaminoethyl groups was inoculated with human fibroblasts at a rate of about $2 \times 10^5$ cells/ml. With slow stirring by a spinner flask, culture was effected at 37° C., pH 7.2 and 20% saturated oxygen concentration for 6 days. On the 1st, 3rd and 5th days, the medium was exchanged. The final number of cells was $3.2 \times 10^6$ cells/ml. Then, the medium was replaced by an Eagle MEM medium containing 100 IU/ml of IFN-β and carboxymethyl cellulose, and incubation was executed at 37° C., pH 7.2 and 20% saturated oxygen concentration for 24 hours. Then, 10 μg/ml of Poly (I).Poly (C) was added, and incubation was executed at 37° C. for 2 hours. Subsequently, the medium was replaced by an Eagle MEM based medium, and 1.0 mM of L-ascorbic acid phosphate was added. Furthermore, culture was executed at 37° C., pH 7.2 and 20% saturated oxygen concentration for 6 days. The quantity of interleukin-6 produced finally was measured by enzymelinked immunosorbent assay. If the relative titer of the product obtained without adding L-ascorbic acid phosphate was 100, the relative titer of the product obtained by adding 1.0 mM of the compound was 120.

Example 4

As done in Example 3, human fibroblasts were cultured, and in a 16-liter tank, $1.7 \times 10^6$ cells/ml were obtained. The medium was then substituted by an Eagle MEM medium containing 100 IU/ml of IFN-β and 0.2% of carboxymethyl cellulose, and incubation was executed at 37° C., pH 7.2 and 20% saturated oxygen concentration for 24 hours. Then, 10 μg/ml of Poly (I).Poly (C) was added, and incubation was executed at 37° C. for 2 hours. Subsequently the medium was replaced by an Eagle MEM based medium, and further by a medium containing 1 g/l of glucose and 0.4 mM of ascorbic acid magnesium phosphate. Aerobic culture was executed for 6 days. During the period, on the 1st and 2nd days, 1 g/l each of gluclose was added, and on the 3rd and 4th days, 0.5 g/l each of gluclose was added. The solution produced from two of the above culture tank was adsorbed by 240 ml of the silica carrier in two columns as done in Example 1. The carrier with the produced solution adsorbed was washed by about one liter each of 1M NaCl solution and sodium phosphate buffer, and IL-6 was recovered by 700 ml of 20 mM hydrochloric acid aqueous solution. Immediately after completion of recovery, the product was neutralized to pH 7.0 by 0.1M trisodium phosphate. The solution was fed through 6 ml of "SP Sephalose FF" (produced by Pharmacia). Then, as done in Example 1, it was adsorbed by 50 ml of "Heparin Toyopearl 650M", and 100 ml of a fraction containing IL-6 was obtained by 20 mM sodium phosphate buffer containing 0.3M NACl. To it, NaCl was added to achieve a final concentration of 3M, and the product was adsorbed by 70 ml of "Phenyl Cellulofine S" (produced by Chisso) in a column. The temperature at the time of adsorption was 30° C. The column was washed by 3M NaCl solution, 20 mM hydrochloric acid solution and sodium phosphate buffer (pH 5.8) in this order, and finally 121 ml of IL-6 solution was recovered by 10 mM sodium phosphate buffer (pH 7.2). The purity of IL-6 in the solution was 98% (reverse phase high performance liquid chromatography), and the yield to the crude produced solution was 57%.

Example 5

As done in Example 4, four lots of purified human IL-6 products were prepared. These purified products were measured on molecular weight distribution by SDS-PAGE, analyzed on N-terminal amino acid sequence and analyzed on sugar composition as done in Example 2. With all the products, the results were the same as those shown in Example 2. The contents of Val-Pro-Pro-Gly-Glu- in the products were 58%, 79%, 78% and 70% respectively.

Example 6

Two liters of an Eagle MEM based medium containing 5% of fetal bovine serum and 3 g/l of crosslinked dextran microcarrier with diethylaminoethyl groups was inoculated with human fibroblasts at a rate of about $2 \times 10^5$ cells/ml. With slow stirring by a spinner flask, culture was executed at 37° C., pH 7.2 and 20% saturated oxygen concentration for 6 days. During the period, on the 1st, 3rd and 5th days, the medium was exchanged. The final number of cells was $3.2 \times 10^6$ cells/ml. Then, the medium was substituted by an Eagle MEM medium containing 100 IU/ml of IFN-β and carboxymethyl cellulose, and incubation was executed at 37° C., pH 7.2 and 20% saturated oxygen concentration for 24 hours. Then, 10 μg/ml of Poly (I).Poly (C) was added, and incubation was executed at 37° C. for 2 hours. Subsequently, the medium was replaced by an Eagle MEM based medium, and 1.0 mM of L-ascorbic acid phosphate was added. Furthermore, culture was executed at 37° C., pH 7.2 and 20% saturated oxygen concentration for 6 days. During this period, on the 1st and 2nd days, 2 g each of glucose was added, and on the 3rd and 4th days, 1 g each of glucose was added. Six days later, the quantity of interleukin-6 produced finally was measured by enzymelinked immunosorbent assay. If the relative titer of the product obtained by adding L-ascorbic acid phosphate only was 100, the relative titer of the product obtained in this case was 120.

Example 7

An IL-6 expression vector with the human IL-6cDNA with the same gene sequence as in the known literature [Nature, 324, 73 (1986)] was constructed as follows with the skeleton obtained from PCR reaction, using the following two DNA oligomers as primers CCGATCGATGCCAG-TACCCCCAGGA and GCCACGGATCCTACATTTGCCGAAG, identified as SEQ ID NO: 4 and SEQ ID NO: 5, respectively, in the Sequence Listing, from the cDNA mixture synthesized by a known method. The amplified DNA was digested by restriction enzymes ClaI and BamHI. Inserting the obtained DNA fragment into claI-BglII site of pKM6, *Escherichia coli* expression vector pKM6IL-6 was obtained. The pKMIL-6 was introduced into *Escherichia coli* HB101, to obtain a recombinant. The recombinant was cultured as follows, to prepare *Escherichia coli*-recombinant human IL-6.

*Escherichia coli* HB101/pKMIL-6 with a human IL-6 expression plasmid was put into 30 liters of a growing medium (containing 0.3% of potassium dihydrogenphosphate, 0.6% of disodium hydrogenphosphate, 0.5% of sodium chloride, 0.1% of ammonium chloride, 0.5% of glucose, 0.5% of casamino acid, 1 mM of magnesium sulfate, 3 µM of ferrous sulfate, 6 µg/ml of vitamin $B_1$ and 50 µg/ml of ampicillin) in a 30-liter jar, and said recombinant was transplanted. The jar was operated at 300 rpm by aerating 1 VVM at 25° C. Indoleacrylic acid as an inducer of tryptophan operon was added, and while glucose and casamino acid were added, culture was executed for 60 hours. The cultured biomass was collected by centrifugation at 10,000 xg for 20 minutes. The biomass was obtained by 895 g. The biomass was suspended in 50 mM Tris hydrochloride buffer (pH 8.0) containing 1 mM EDTA and 100 mM NaCl, to achieve 20 as OD 550 nm. The biomass was crushed by Mantongallin and centrifuged, and the crushed extract was recovered. The extract contained 235 g of proteins and 495 mg of IL-6. In this case, the quantity of IL-6 was measured by the ELISA method shown in Example 1.

The extract was adsorbed by 5.5 liters of the silica carrier used in Example 1, and the carrier was washed by sodium phosphate buffer (pH 7.2). Then, 20 mM hydrochloric acid aqueous solution was used to recover 462 mg of IL-6. To the eluate, ammonium sulfate was added to achieve a final concentration of 1.33M, and the insoluble impurities were removed by centrifugation. Then, the residue was adsorbed by 200 ml of a butyl carrier ("Butyl Toyopearl 650M" produced by Tosoh), and the carrier was washed by 20 mM of hydrochloric acid. Then, 10 mM sodium phosphate buffer was used to recover 237 mg of IL-6 of 84% in purity according to SDS-PAGE purity detection method. The eluted IL-6 was directly adsorbed by 80 ml of a heparin carrier ("AF-heparin Toyopearl 650M" produced by Tosoh), and recovered by a solution with 0.3M NaCl contained in 20 mM sodium phosphate buffer (pH 7.2), to obtain 114 mg of IL-6 of 91% in purity. The eluate was further purified again by 200 ml of the same butyl carrier as used above, to obtain 66 mg of human IL-6. The obtained IL-6 was 95% or more in purity (analyzed by $C_{18}$ reverse phase high performance liquid chromatography).

INDUSTRIAL APPLICABILITY

The present invention allows the utilization of compositions containing IL-6 with sugar chains useful as medicines. The IL-6 compositions of the present invention are useful as remedies generally for immune deficiency, bone marrow inhibition after bone marrow transplantation and chemotherapy, thrombocytopenia, etc. Furthermore, they can be used as standards for measuring the IL-6 concentration in blood, etc.

Moreover, according to the process described in the present invention, high quality IL-6 can be massproduced, and furthermore, IL-6 can be highly purified. In addition, the production scale can be expanded to allow industrial application.

---

We claim:

1. A process for preparing human interleukin-6, comprising culturing human interleukin-6 producing cells in a medium, and adding ascorbic acid or any of its derivatives into the medium.

2. A process for preparing human interleukin-6, according to claim 1, wherein the human interleukin-6 producing cells are human fibroblasts.

3. A process for preparing human interleukin-6, according to claim 2, wherein a sugar is further added to the medium.

4. A process for preparing human interleukin-6, comprising purifying the interleukin-6 from a crude and concentrated interleukin-6 solution by heparin carrier chromatography.

5. A process for preparing human interleukin-6, according to claim 4, further comprising a purification step utilizing a hydrophobic carrier and a silica based adsorbent.

6. A process for preparing human interleukin-6 according to claim 5, wherein comprising the steps in the order below of 1) purifying the interleukin-6 through silica based adsorbent chromatography, 2) further purifying the interleukin-6 through heparin carrier chromatography, and 3) further purifying the interleukin-6 by chromatography with a hydrophobic carrier.

7. A process for preparing human interleukin-6, according to claim 6, wherein human interleukin-6 is obtained by culturing human fibroblasts.

8. A process for preparing human interleukin-6 according to claim 4, further comprising a purification step utilizing a hydrophobic carrier.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

Pro  Val  Pro  Pro  Gly
        1                        5

( 2 ) INFORMATION FOR SEQ ID NO:2:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:2:

Val Pro Pro Gly Glu
1               5

(2) INFORMATION FOR SEQ ID NO:3:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:3:

Ala Pro Val Pro Pro
1               5

(2) INFORMATION FOR SEQ ID NO:4:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (ix) FEATURE:
    (A) NAME/KEY: misc_feature
    (B) LOCATION: 1..25
    (D) OTHER INFORMATION: /function="primer"

(xi) SEQUENCE DESCRIPTION: SEQ ID NO:4:

CCGATCGATG CCAGTACCCC CAGGA                25

(2) INFORMATION FOR SEQ ID NO:5:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO -continued

```
( i x ) FEATURE:
        ( A ) NAME/KEY: misc_feature
        ( B ) LOCATION: 1..25
        ( D ) OTHER INFORMATION: /function="primer"

( x i ) SEQUENCE DESCRIPTION: SEQ ID NO:5:

GCCACGGATC CTACATTTGC CGAAG                                                            25
```